US012599744B2

(12) United States Patent
O'Donnell et al.

(10) Patent No.: US 12,599,744 B2
(45) Date of Patent: Apr. 14, 2026

(54) DRAINAGE MEMBER DESIGN AND ULTRASONIC WELDING METHOD FOR ATTACHMENT OF CATHETER TUBE TO DRAINAGE MEMBER

(71) Applicant: Hollister Incorporated, Libertyville, IL (US)

(72) Inventors: Paul M. O'Donnell, Castlebar (IE); Joseph Fahey, Newport (IE)

(73) Assignee: Hollister Incorporated, Libertyville, IL (US)

( * ) Notice: Subject to any disclaimer, the term of this patent is extended or adjusted under 35 U.S.C. 154(b) by 503 days.

(21) Appl. No.: 17/999,555

(22) PCT Filed: May 4, 2021

(86) PCT No.: PCT/US2021/030688
§ 371 (c)(1),
(2) Date: Nov. 21, 2022

(87) PCT Pub. No.: WO2021/242487
PCT Pub. Date: Dec. 2, 2021

(65) Prior Publication Data
US 2023/0191079 A1      Jun. 22, 2023

Related U.S. Application Data

(60) Provisional application No. 63/031,050, filed on May 28, 2020.

(51) Int. Cl.
*A61M 25/00*      (2006.01)
*A61M 27/00*      (2006.01)

(52) U.S. Cl.
CPC .... *A61M 25/0017* (2013.01); *A61M 25/0014* (2013.01); *A61M 25/0045* (2013.01); *A61M 27/00* (2013.01)

(58) Field of Classification Search
CPC .......... A61M 25/0017; A61M 25/0014; A61M 25/0045; A61M 27/00; A61M 2025/0046;
(Continued)

(56) References Cited

U.S. PATENT DOCUMENTS 3,602,228 A      8/1971  Cowley
3,849,871 A  *  11/1974  Kaunitz ................. B23K 28/02
228/256
(Continued)

FOREIGN PATENT DOCUMENTS

DE        3434015 C2  *  7/1987  ......... B29C 66/5229
EP        0616817 A1      9/1994
(Continued)

OTHER PUBLICATIONS

International Search Report and Written Opinion for PCT/US2021/030688 Dated Sep. 23, 2021.

*Primary Examiner* — Adam Marcetich

(74) *Attorney, Agent, or Firm* — Cook Alex Ltd.

(57)      ABSTRACT

A urinary catheter is disclosed. The urinary catheter comprises a catheter tube having a proximal insertion end and a distal end. The catheter also comprises a drainage member. The drainage member includes a wall having an inner surface and an outer surface. The inner surface defines a drainage lumen having an opening in a proximal end of the drainage member. The distal end of the catheter tube is inserted through the opening of the proximal end of the drainage member and is located in the lumen. The wall of the drainage member has at least one window therethrough. The drainage member and the catheter tube are welded to one another at one or more welding sites in the vicinity of the window(s).

15 Claims, 4 Drawing Sheets

(58) Field of Classification Search

CPC ...... A61M 25/0097; A61M 2210/1089; A61M 25/0009; B29C 66/5221; B29C 66/81429; B29C 66/81433; B29C 66/8322; B29C 66/83221; B29C 65/08; B29C 66/65; B29C 66/73921; B29L 2023/005; B29L 2023/006; B29L 2023/007; B23K 20/10; B23K 20/106

See application file for complete search history.

(56) References Cited

U.S. PATENT DOCUMENTS

| | | | | |
|---|---|---|---|---|
| 3,966,520 | A * | 6/1976 | Fallenbeck | B29C 66/73921 228/1.1 |
| 3,982,980 | A * | 9/1976 | van Manen | B29C 66/8322 156/244.18 |
| 4,670,207 | A * | 6/1987 | Yamada | B29C 66/1226 156/322 |
| 4,701,162 | A | 10/1987 | Rosenberg | |
| 5,356,391 | A | 10/1994 | Stewart | |
| 5,674,209 | A | 10/1997 | Yarger | |
| 5,879,333 | A * | 3/1999 | Smith | A61M 25/0097 604/164.04 |
| 5,919,170 | A | 7/1999 | Woessner | |
| 5,989,240 | A | 11/1999 | Strowe | |
| 6,016,948 | A * | 1/2000 | Kurotobi | B23K 9/0026 219/137.9 |
| 7,799,153 | B2 | 9/2010 | Stenzel | |
| 9,078,682 | B2 | 7/2015 | Lenker et al. | |
| 2003/0105453 | A1 * | 6/2003 | Stewart | B29C 66/12445 604/537 |
| 2008/0091145 | A1 * | 4/2008 | House | A61M 25/002 604/171 |
| 2008/0293999 | A1 | 11/2008 | Halahmi | |
| 2011/0060317 | A1 * | 3/2011 | Frojd | A61M 25/0009 29/428 |
| 2014/0341642 | A1 * | 11/2014 | Kawasaki | B23K 9/325 403/271 |
| 2017/0045163 | A1 * | 2/2017 | Popov | F16L 25/14 |
| 2017/0129001 | A1 * | 5/2017 | Bouey | F16L 13/146 |
| 2017/0340860 | A1 * | 11/2017 | Eberhardt | B29C 65/1412 |
| 2018/0111327 | A1 * | 4/2018 | Watanabe | B29C 66/114 |
| 2019/0010961 | A1 * | 1/2019 | Kumaou | B06B 1/02 |
| 2019/0022367 | A1 | 1/2019 | Burkholz et al. | |
| 2019/0358435 | A1 | 11/2019 | Andersin et al. | |
| 2019/0381275 | A1 * | 12/2019 | Mintz | A61M 25/0014 |

FOREIGN PATENT DOCUMENTS

| | | | |
|---|---|---|---|
| EP | 2292294 | A1 | 3/2011 |
| EP | 2545953 | A1 | 1/2013 |
| GB | 215452 | A | 5/1924 |
| WO | 199808562 | A1 | 3/1998 |
| WO | 2002053070 | A1 | 7/2002 |
| WO | 2006125241 | A1 | 11/2006 |
| WO | 2013127718 | A1 | 9/2013 |
| WO | 2019123003 | A1 | 6/2019 |
| WO | 2019123005 | A1 | 6/2019 |

* cited by examiner

DRAINAGE MEMBER DESIGN AND ULTRASONIC WELDING METHOD FOR ATTACHMENT OF CATHETER TUBE TO DRAINAGE MEMBER

The present application is the U.S. National Stage Application of PCT Application No. PCT/US2021/030688, filed May 4, 2021, which claims the benefit of and priority to U.S. Provisional Application No. 63/031,050, filed May 28, 2020, all of which is hereby incorporated herein by reference.

BACKGROUND

Field of the Disclosure

The present disclosure generally relates to catheter assemblies. More particularly, the present disclosure relates to catheter assemblies that include a drainage member attached to the catheter tube.

Description of Related Art

Intermittent urinary catheters may comprise a catheter tube joined to a funnel for the drainage of urine out of the catheter tube. The tube is inserted into a user's urethra and urine drains through a lumen of the tube. Typically, a drainage member, such as a funnel, is attached to the distal end of the catheter tube. The drainage member may be used to direct urine to a waste receptacle or may serve as a connector to a collection system, such as a urine collection bag. There is a need for an improved urinary catheter having a strong and stable connection between the tube and the funnel.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, a urinary catheter is disclosed. The urinary catheter comprises a catheter tube having a proximal insertion end and a distal end. The catheter also comprises a drainage member. The drainage member includes a wall having an inner surface and an outer surface. The inner surface defines a drainage lumen having an opening in a proximal end of the drainage member. The distal end of the catheter tube is inserted through the opening of the proximal end of the drainage member and is located in the lumen. The wall of the drainage member has at least one window therethrough. The drainage member and the catheter tube are welded to one another at one or more welding sites in the vicinity of the window(s).

In another aspect, a drainage member is disclosed. The drainage member comprises a wall having an inner surface and an outer surface. The wall has at least one window therethrough. The inner surface defines a drainage lumen having an opening in a proximal end of the drainage member. The opening is configured to receive a distal end of a catheter tube. The drainage member is configured to be welded to the catheter tube at one or more welding sites in the vicinity of the window(s).

In another aspect a method for constructing a catheter assembly is disclosed. The method comprises a step of providing a drainage member having at least one window therethrough. The drainage member is welded to a catheter tube through the at least one window.

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

Figures 1, 2:
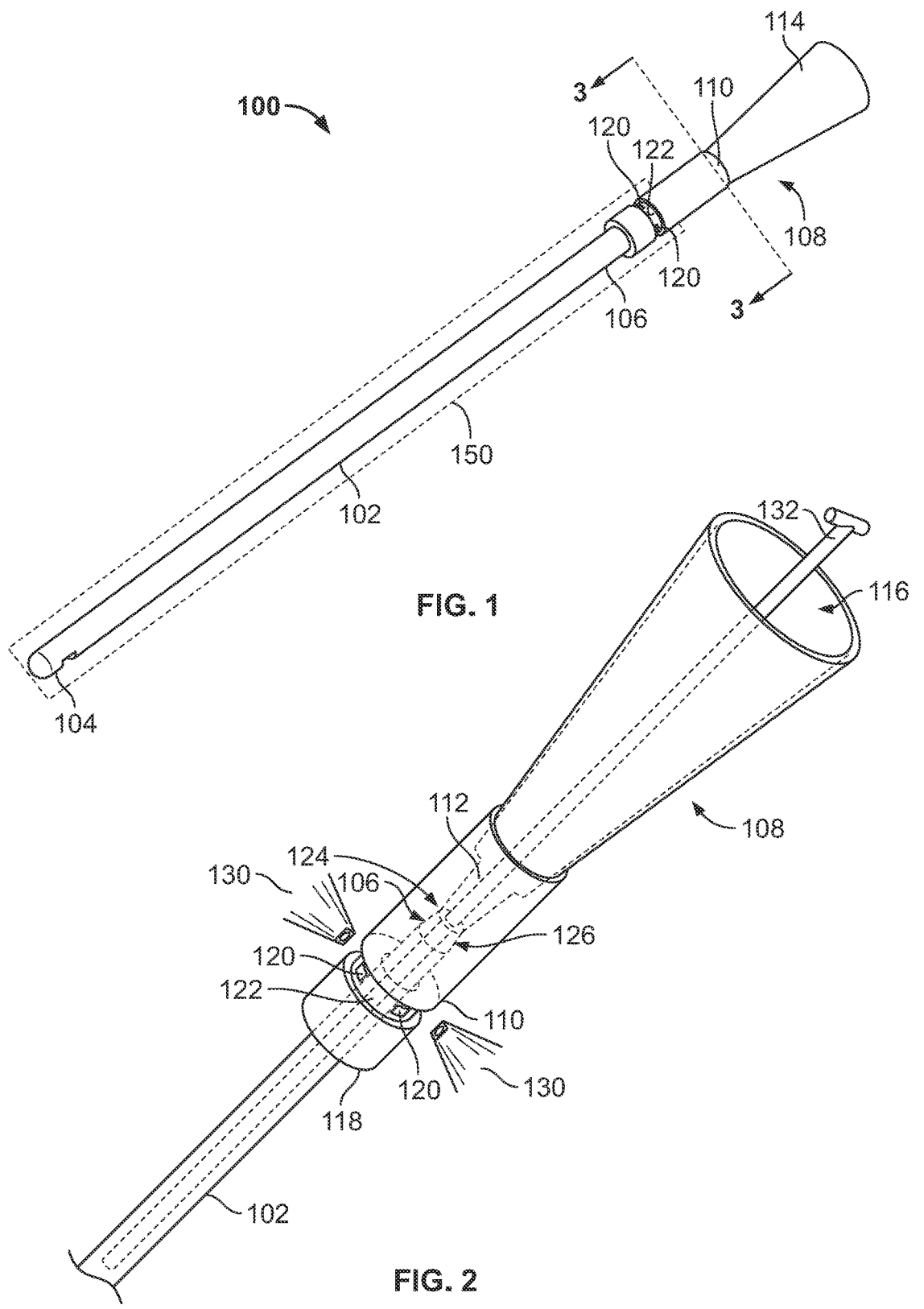
FIG. 1 is a perspective view of an embodiment of a urinary catheter, showing the catheter inside an optional sleeve.
FIG. 2 is an enlarged perspective sectional view of the urinary catheter of FIG. 1, showing the catheter tube and drainage member being connected by spot-welders.

Catheter assemblies according to the present disclosure and their individual components may be variously configured without departing from the scope of the present disclosure, but in one embodiment, a urinary catheter is configured as shown in FIG. 1.

FIG. 1 shows an embodiment of a urinary catheter 100. The urinary catheter 100 comprises a catheter tube 102 having a proximal insertion end 104 and a distal end 106. The catheter 100 also comprises a drainage member 108. The drainage member 108 includes a wall 110 having an inner surface 112 (shown in FIGS. 2 and 3) and an outer surface 114. The drainage member 108 is shown by itself in FIG. 4. Referring to FIGS. 1 and 2, the wall 110 of the drainage member 108 has at least one window 120 therethrough. In the illustrated embodiment, the wall 110 has two windows 120 therethrough. Alternative embodiments may have any appropriate number of windows. In the embodiment shown, the windows 120 are square-shaped. In alternative embodiments, any other appropriate shape may be used for the windows, for example the windows may be polygonal or have a substantially circular shape. The drainage member 108 and the catheter tube 102 are welded to one another at one or more welding sites in the vicinity of the window(s) 120. The catheter tube 102 and the drainage member 108 may be ultrasonically welded together. In the embodiment shown in FIGS. 1 and 2, the outer surface 114 of the wall 110 of the drainage member 108, optionally, includes a recess 122. As shown, the windows 120 may be located in the recess(es). Alternative embodiments may have more than one recess. For instance, the wall 110 of the drainage member 108 may include one recess 122 that contains all of the windows 120, or in an alternative, the wall 110 of the drainage member 108 may include two or more recesses 122, wherein each recess 122 may contain one or more windows 120.

As shown in FIG. 1, the urinary catheter 100, optionally, may further include a sleeve 150 (shown in broken line) surrounding the catheter tube 102. The sleeve 150 may also cover the one or more recesses 122 and the windows 120. For example, the distal end of the sleeve 150 may be attached to the drainage member 108 at a location that is distal of the windows and/or recesses. The sleeve 150 covers and protects the welding sites after the catheter tube 102 and drainage member 108 have been welded together. The sleeve may be made of any appropriate protective material, including plastic polymers such as low-density polyethylene.

FIG. 2 shows the urinary catheter of FIG. 1 and illustrates the interior and exterior connections between the catheter tube 102 and the drainage member 108. As shown in FIG. 2, one connection between the catheter tube 102 and the drainage member 108 is a welded connection. Welding tools 130 are used to spot-weld the catheter tube 102 to the drainage member 108. The windows 120 are configured to allow each welding tool 130 to spot-weld the drainage member 108 to the catheter tube 102 at or in the vicinity of the windows 120. The welding tools 130 are brought up to and/or inserted through each window 120 such that each individual welding tool is positioned to form a weld between the catheter tube 102 and the drainage member 108. If a recess 122 is present, the tool 130 is inserted into the recess 122 to access the window 120. The welding tool 130 is then actuated to 130 spot weld a surface of the drainage member 108 to a surface of the catheter tube 102, resulting in a weld-tight bond between the tube 102 and the drainage member 108. In one alternative, the welding tool 130 is an ultra-sonic welder, so that the spot welds are ultra-sonic spot welds. In alternative embodiments, the welding tool may be any other type of appropriate known welder.

Still referring to FIG. 2, a protective instrument 132, such as the illustrated welding mandrel may be employed to assist in the welding process. Optionally, the welding mandrel outer diameter may substantially match the inner lumen diameter of the catheter tube 102. In other alternatives, the outer diameter of the welding mandrel may be larger or smaller than the inner diameter of the catheter tube's lumen. The protective instrument 132 is inserted through the lumen 116 of the drainage member 108 and into a drainage lumen 128 of the urinary catheter 100. The protective instrument 132 is configured to prevent the welding tools 130 from penetrating too far into the outer wall of the lumen 128 and damaging the catheter tube 102 and/or the drainage member 108. Though a welding mandrel is shown, any other known protective instrument, configured to stop the welding tools from advancing through the lumen 116 and damaging the catheter 100 may be used.

Figure 3:
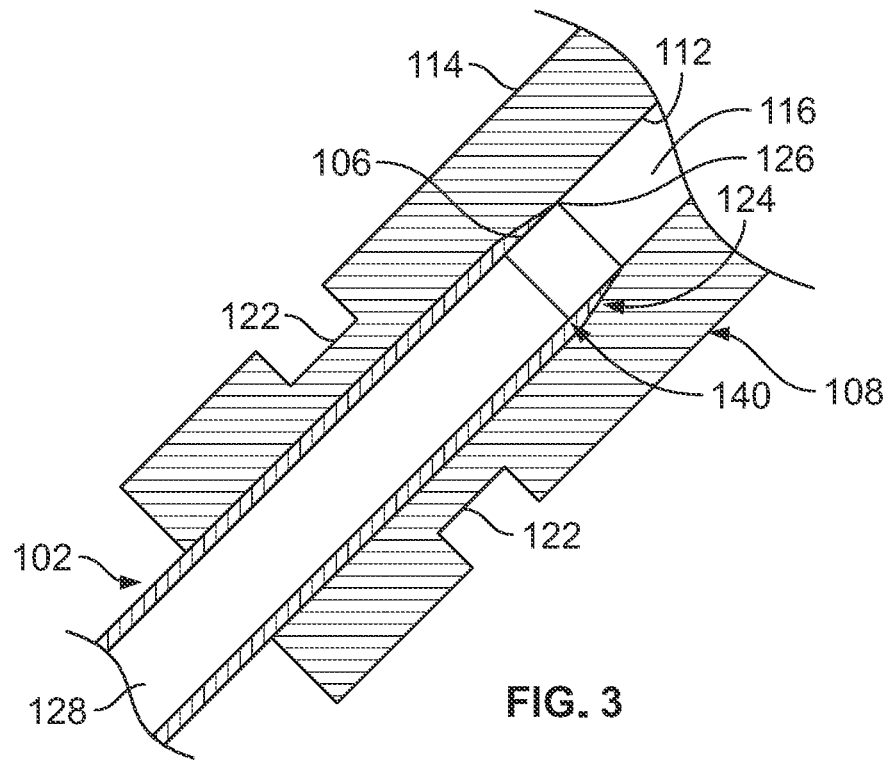
FIG. 3 is an enlarged cross-sectional view of the urinary catheter of FIG. 1, showing the catheter tube and drainage member connected after welding.
Figure 4:
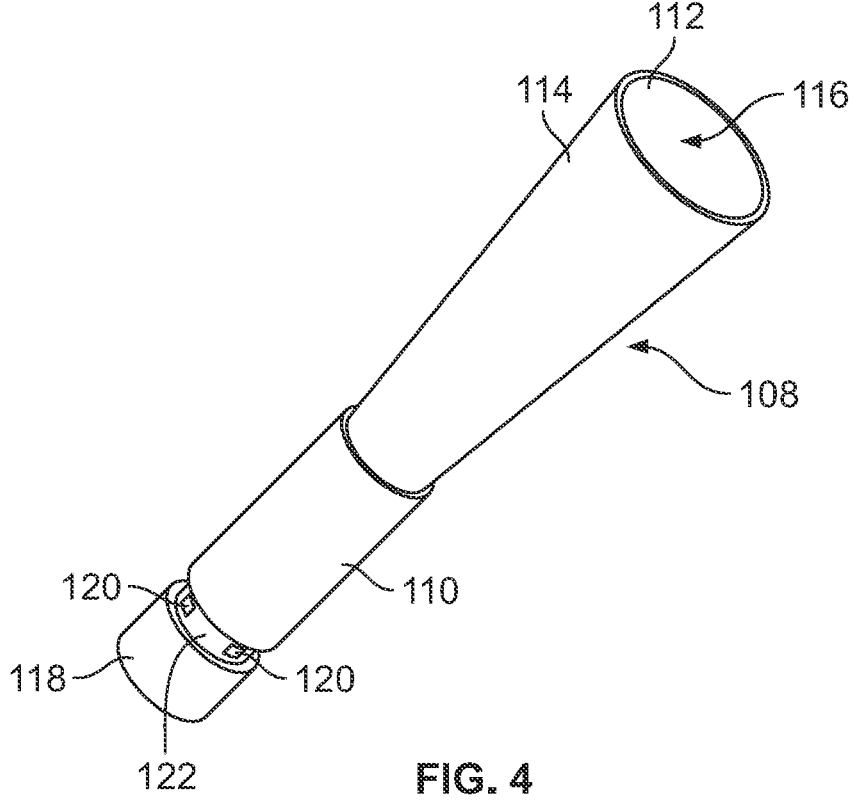
FIG. 4 is a perspective view of the drainage member of FIG. 1.

FIGS. 2 and 3 also show a detailed view of the inner surface 112 of the drainage member 108. The inner surface 112 defines the drainage lumen 116 having an opening in a proximal end 118 of the drainage member 108. The distal end 106 of the catheter tube 102 may be inserted through the opening of the proximal end 118 of the drainage member

108, such that the distal lumen 128 of tube 102 is located close to and in alignment with the lumen 116, forming a fluid connection between the drainage lumen 116 of the drainage member 108 and the lumen 128 of the catheter 102. The drainage member 108 includes an inner structure 124 within the lumen 116 that may be mechanically engaged with the outer diameter of the distal end 106 of the catheter tube 102. The mechanical engagement forms an interference fit between the outer surface of the catheter tube 102 and the inner surface 112 of the drainage member 108. The mechanical engagement between the distal end 106 of the catheter tube 102 and the inner structure 124 may form a liquid-tight seal.

In the embodiment shown, a tapered section 126 of the inner surface 112 of the drainage member 108 defines the inner structure 124. At least a segment of the tapered section 126 may have an inner diameter that is less than an outer diameter of the catheter tube 102. When the distal end 106 of the catheter tube 102 is located within a segment of the tapered section 126, the distal end 106 of the catheter tube is crimped or squeezed by the tapered section 126. Optionally, the dimensions and tolerances of the distal end 102 of the catheter tube 102 and the tapered section 126 are such that the outer diameter of the catheter tube's distal end is crimped without any changes or significant changes to the inner diameter of the catheter tube 106. Additionally, in one alternative embodiment, the diameter of the lumen 116 of the drainage member 108 is equal to or greater than the lumen of the catheter tube 102.

In FIG. 3, the inner structure 124 of the drainage member including the tapered section 126 is shown such that a union point 140 between the catheter distal end 106 and the inner structure 124 is visible. The connection between the catheter tube 102 and the tapered section 126 results in a mechanical engagement, such as an interference fit. The mechanical engagement between the distal end 106 of the catheter tube 102 and the tapered section 126 may form a liquid-tight seal under normal use conditions. Thus, there are two connections between the catheter tube 102 and the drainage member 108, a welded connection and a mechanical connection. The mechanical engagement provides an interference fit and a fluid tight seal between the interior of the drainage member and the catheter tube, while the welding provides bonding between the catheter tube and drainage member.

Figure 3A:
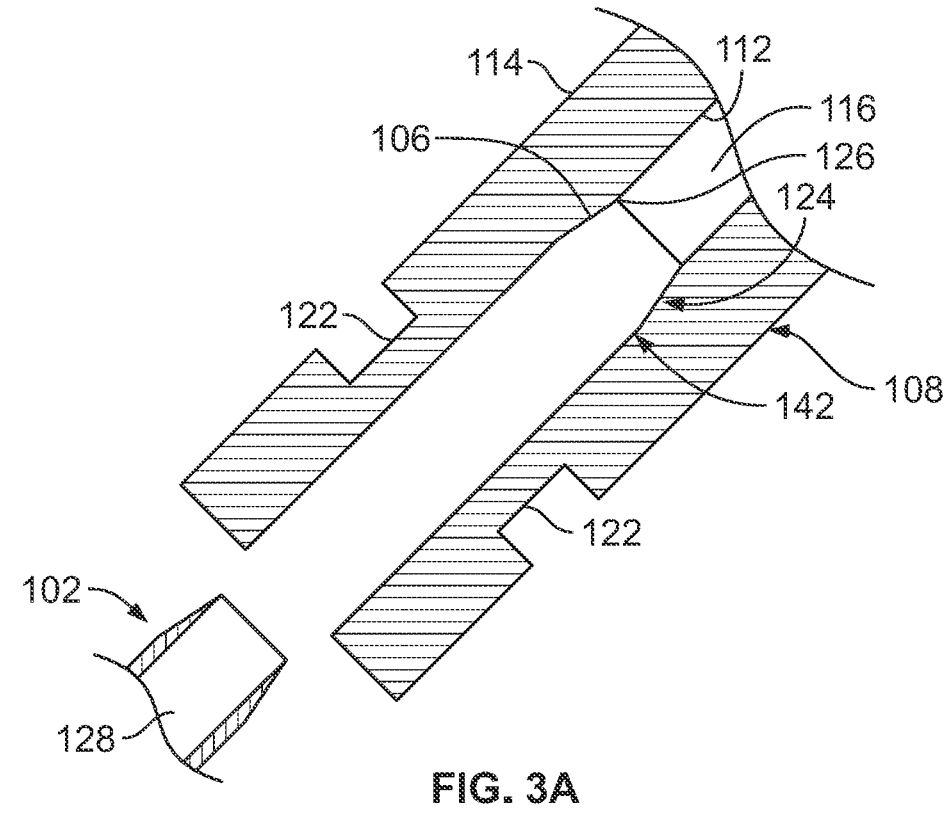
FIG. 3A is an enlarged cross-sectional view of the urinary catheter of FIG. 1, showing the catheter tube and drainage member, the tube having a conical shaped taper and the drainage member having a conical seat.

As shown in FIG. 3A, in an alternative embodiment, a conical-shaped taper 142 may be formed onto the distal end portion 106 of the catheter tube 102. The conical taper 142 may be formed by any appropriate method including being ground into the tube or heat formed. The conically tapered tube may mate with a conical seat or taper 126 formed in the drainage member.

Figure 3B:
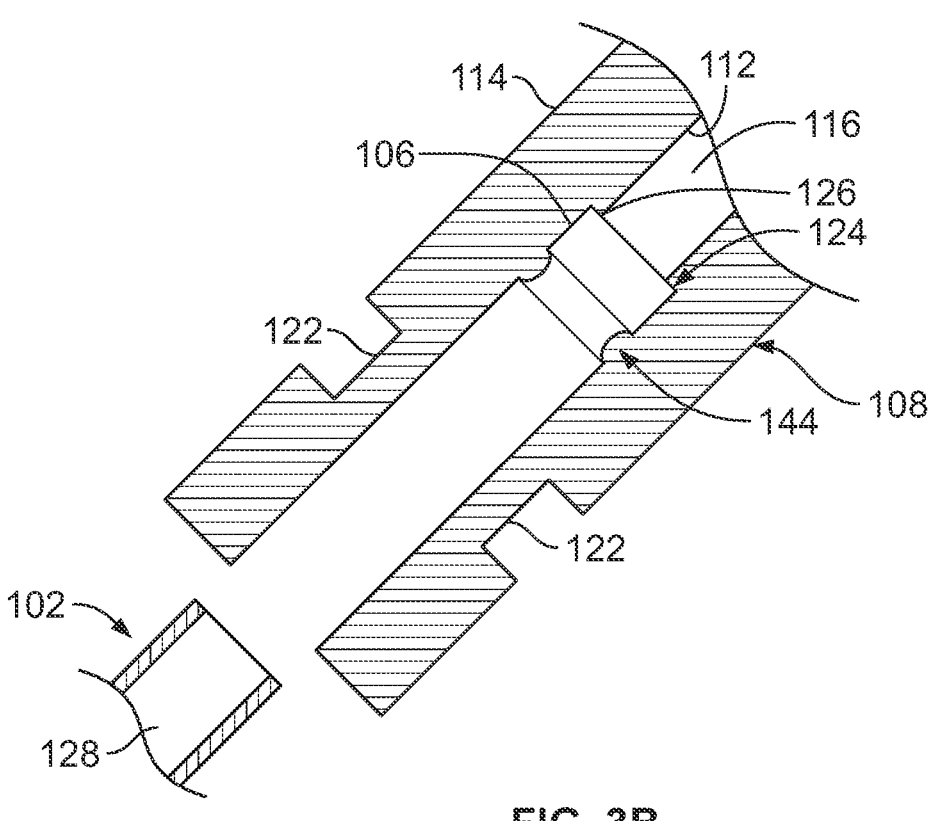
FIG. 3B is an enlarged cross-sectional view of the urinary catheter of FIG. 1, showing the catheter tube and drainage member, the drainage member inner lumen diameter (port) having protrusions.

As shown in FIG. 3B, in another alternative embodiment, one or more sealing rings 144 may be formed on the inner surface 112 defining the proximal inner lumen (port) of the drainage member. The rings 144 may protrude into the lumen of the drainage member and contact the distal end of the catheter tube 102. Optionally, the inner diameter of the protruding rings 144 may be calculated by the equation of Protrusion Inner Diameter=MinTubeOD-0.05 mm, wherein MinTubeOD is the outer diameter of tube 102. Alternatively, or in addition to rings on the inner surface of the drainage member, one or more rings (not shown) could be on the outer surface of the distal end portion of the catheter tube 102. The rings on the catheter tube contact the inner surface 112 defining the lumen of the drainage member to form a mechanical connection.

In an embodiment, the external width of the drainage member 108 at the tapered section may be 7.50 millimeters (mm). Additionally, the minimum depth of the recess is 0.5 mm. The inner diameter of the tapered section (TaperID), where the catheter tube intersects with the drainage member may be calculated by the equation of TaperID=MaxTubeOD−MinTubeOD−0.05 mm. In addition to these dimensions, other appropriate dimensions may be used for the width of the drainage member, the width of the tapered section, the inner diameter of the tapered section and the height of the recess.

The drainage members disclosed herein may be, in one example, made by injection molding. In addition to injection molding, other appropriate ways to manufacture the drainage member may be used. The drainage member may be made of any appropriate material known to one of ordinary skill in the art including low-density polyethylene (LDPE), TPE, PU, or other polymeric materials.

Figures 5, 6:
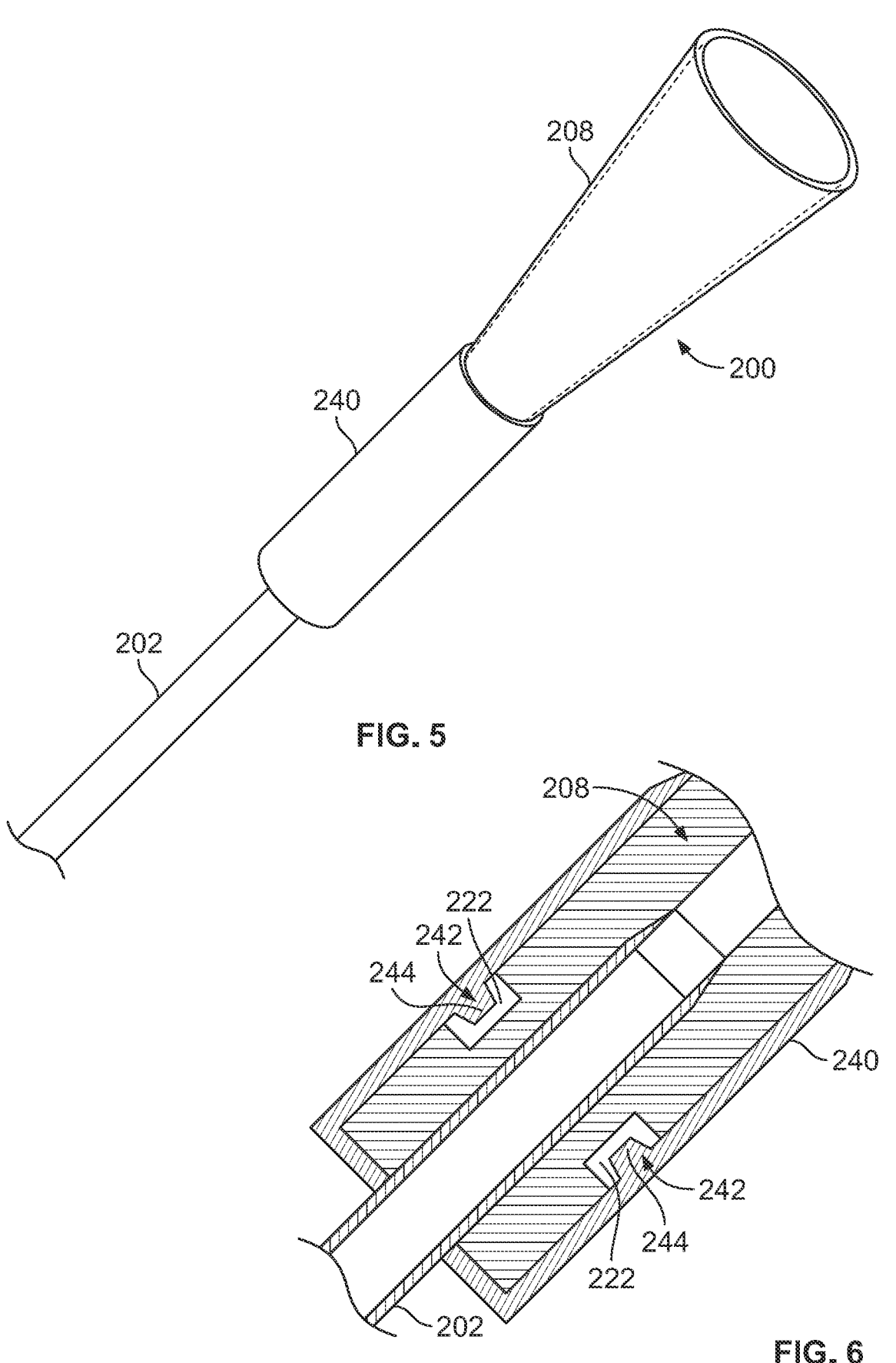
FIG. 5 is a perspective view of an embodiment of a urinary catheter having a gripping member.
FIG. 6 is a cross-sectional view of the urinary catheter of FIG. 5, showing a segment of the catheter having the gripping member.

In the embodiments shown in FIGS. 5 and 6, a urinary catheter 200 may further include a gripping member 240 (gripper) for gripping the catheter during use. The gripper 240 may be releasably attached to the drainage member 208. The gripper 240 also may contact the catheter tube 202. As shown in FIG. 6, the gripping member includes two protrusions 242 configured to engage a respective recess 222. Each protrusion comprises a barb 244 and the barb 244 engages the recess 222. The protrusion(s) may be configured to engage the recess(es) so as to releasably attach the gripper 240 to the drainage member 208. Though two protrusions and barbs are shown in FIG. 6, any appropriate number of protrusions and barbs, may be used in alternative embodiments of the gripper. The gripper 240 may be made of an appropriate grip-able and flexible material, such as TPE. The gripper 240 enables a user to more easily handle the urinary catheter 200 during use and prevents the catheter from slipping or falling out of a user's hand.

In all embodiments described above, and in all alternative embodiments, the catheters may be, but are not limited to, hydrophilic catheters. Additionally, parts of the catheter tube may include a hydrophilic coating. When the hydrophilic coating is wetted or hydrated with a hydration medium, such as water, it becomes lubricious. The lubricity eases introduction of the device into the body and aids in reducing pain and discomfort associated with such introduction. The hydrophilic coating can be a single layer or a multilayer hydrophilic coating. Multi-layered coating can include at least a base coat and a top layer. The hydrophilic coating may be placed on at least one of the catheter tube outer surface and the catheter tube inner surface. In other embodiments that do not include a hydrophilic coating, the catheter may have a lubricious gel on the outer surface of the catheter. The hydrophilic coating may be placed on the catheter shaft inner surface. When the inner surface is coated, the hydrophilic coating may increase fluid flow rate.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A urinary catheter, comprising:
   a catheter tube having a proximal insertion end and a distal end;
   a drainage member including a wall having an inner surface and an outer surface, the inner surface defining a drainage lumen having an opening in a proximal end of the drainage member;
   the distal end of the catheter tube being inserted through the opening of the proximal end of the drainage member and located in the lumen, the wall of the drainage member having an outer surface that includes a recess, a plurality of windows through the wall of the drainage member and being located in the recess, wherein the drainage member and the catheter tube are welded to one another at the plurality of windows.

2. The urinary catheter of claim 1, wherein the catheter tube and the drainage member are ultrasonically welded together.

3. The urinary catheter of claim 1, wherein the windows of the plurality of windows are configured to allow a welding tool to spot-weld the drainage member to the tube.

4. The urinary catheter of claim 1, wherein the drainage member includes an inner structure within the lumen that is mechanically engaged with the distal end of the catheter tube.

5. The urinary catheter of claim 4, wherein the inner structure comprises a tapered section of the inner surface of the drainage member.

6. The urinary catheter of claim 5, wherein a segment of the tapered section has an inner diameter that is less than an outer diameter of the catheter tube.

7. The urinary catheter of claim 5, wherein the distal end of the catheter tube is located within a segment of the tapered section.

8. The urinary catheter of claim 7, wherein the mechanical engagement between the distal end of the catheter tube and the tapered section forms a liquid-tight seal.

9. The urinary catheter of claim 4, wherein the mechanical engagement between the distal end of the catheter tube and the inner structure forms a liquid-tight seal.

10. The urinary catheter of claim 1, further including a sleeve surrounding the entire catheter tube, the sleeve being attached to the drainage member and covering the recess and plurality of windows.

11. The urinary catheter of claim 1, wherein the catheter tube further includes a hydrophilic coating on at least one of an outer surface and an inner surface of the catheter tube.

12. The urinary catheter of claim 1, wherein the catheter tube includes a gel on an outer surface of the catheter.

13. A urinary catheter, comprising:
   a catheter tube having a proximal insertion end and a distal end;
   a drainage member including a wall having an inner surface and an outer surface, the inner surface defining a drainage lumen having an opening in a proximal end of the drainage member;
   the distal end of the catheter tube being inserted through the opening of the proximal end of the drainage member and located in the lumen, the wall of the drainage member having at least one window therethrough, wherein the drainage member and the catheter tube are welded to one another at a site of the window(s); and
   a gripper for gripping the catheter tube when using the urinary catheter, wherein the gripper is releasably attached to the drainage member.

14. The urinary catheter of claim 13, wherein the outer surface of the wall of the drainage member includes one or more recesses and the gripper includes a protrusion that is configured to engage the one or more recesses so as to releasably attach the gripper to the drainage member.

15. The urinary catheter of claim 14, wherein the protrusion comprises a barb and the barb engages the one or more recesses.

\*    \*    \*    \*    \*